United States Patent
Shrivastava et al.

(10) Patent No.: US 10,335,364 B2
(45) Date of Patent: Jul. 2, 2019

(54) COMPOSITION FOR TOPICAL APPLICATION COMPRISING GLYCEROL AND TANNINS

(71) Applicants: Remi Shrivastava, Cebazat (FR); Lea Shrivastava, Cebazat (FR); Ravi Shrivastava, Cebazat (FR)

(72) Inventors: Remi Shrivastava, Cebazat (FR); Lea Shrivastava, Cebazat (FR); Ravi Shrivastava, Cebazat (FR)

(*) Notice: Subject to any disclaimer, the term of this patent is extended or adjusted under 35 U.S.C. 154(b) by 227 days.

(21) Appl. No.: 15/426,287

(22) Filed: Feb. 7, 2017

(65) Prior Publication Data
US 2017/0151172 A1 Jun. 1, 2017

Related U.S. Application Data

(63) Continuation of application No. 14/896,006, filed as application No. PCT/EP2013/061835 on Jun. 7, 2013, now Pat. No. 9,597,298.

(51) Int. Cl.
| | | |
|---|---|---|
| *A61K 36/00* | (2006.01) | |
| *A61K 9/00* | (2006.01) | |
| *A61K 47/10* | (2017.01) | |
| *A61K 9/10* | (2006.01) | |
| *A61K 8/34* | (2006.01) | |
| *A61K 8/60* | (2006.01) | |
| *A61Q 19/00* | (2006.01) | |
| *A01N 1/02* | (2006.01) | |
| *A61K 45/06* | (2006.01) | |
| *A61K 31/00* | (2006.01) | |
| *A61K 31/047* | (2006.01) | |
| *A61K 9/70* | (2006.01) | |
| *A61K 47/46* | (2006.01) | |

(52) U.S. Cl.
CPC .......... *A61K 9/0014* (2013.01); *A01N 1/0221* (2013.01); *A61K 8/345* (2013.01); *A61K 8/602* (2013.01); *A61K 9/006* (2013.01); *A61K 9/0034* (2013.01); *A61K 9/0043* (2013.01); *A61K 9/10* (2013.01); *A61K 9/7007* (2013.01); *A61K 31/00* (2013.01); *A61K 31/047* (2013.01); *A61K 45/06* (2013.01); *A61K 47/10* (2013.01); *A61K 47/46* (2013.01); *A61Q 19/00* (2013.01)

(58) Field of Classification Search
CPC ...................................................... A61K 36/00
USPC ........................................................ 424/725
See application file for complete search history.

(56) References Cited

U.S. PATENT DOCUMENTS

| 3,923,984 A | 12/1975 | Zuercher |
| 2008/0213300 A1 | 9/2008 | Jochim et al. |

FOREIGN PATENT DOCUMENTS

| DE | 20310234 U1 | 9/2003 |
| FR | 2768342 A1 | 3/1999 |
| JP | 2003238435 A | 8/2003 |
| RU | 2287324 C1 | 11/2006 |

OTHER PUBLICATIONS

International Search Report for PCT/EP2013/061835 dated Jul. 17, 2013.
English translation of the Abstract for JP 2003238435 published on Aug. 27, 2003.
English translation of the Abstract for FR 2768342 published on Mar. 19, 1999.
English translation of the Abstract for DE 20310234 published on Sep. 18, 2003.
English translation of RU 2287324 published Nov. 20, 2006.

*Primary Examiner* — Michael V Meller
(74) *Attorney, Agent, or Firm* — Thomas|Horstemeyer, LLP

(57) ABSTRACT

A preparation for topical application comprising glycerol and plant tannins, wherein the plant tannins have the capacity to bind to glycerol so that the glycerol has filmogen quality.

1 Claim, 5 Drawing Sheets

COMPOSITION FOR TOPICAL APPLICATION COMPRISING GLYCEROL AND TANNINS

CROSS-REFERENCE TO RELATED APPLICATION

Figure 1:
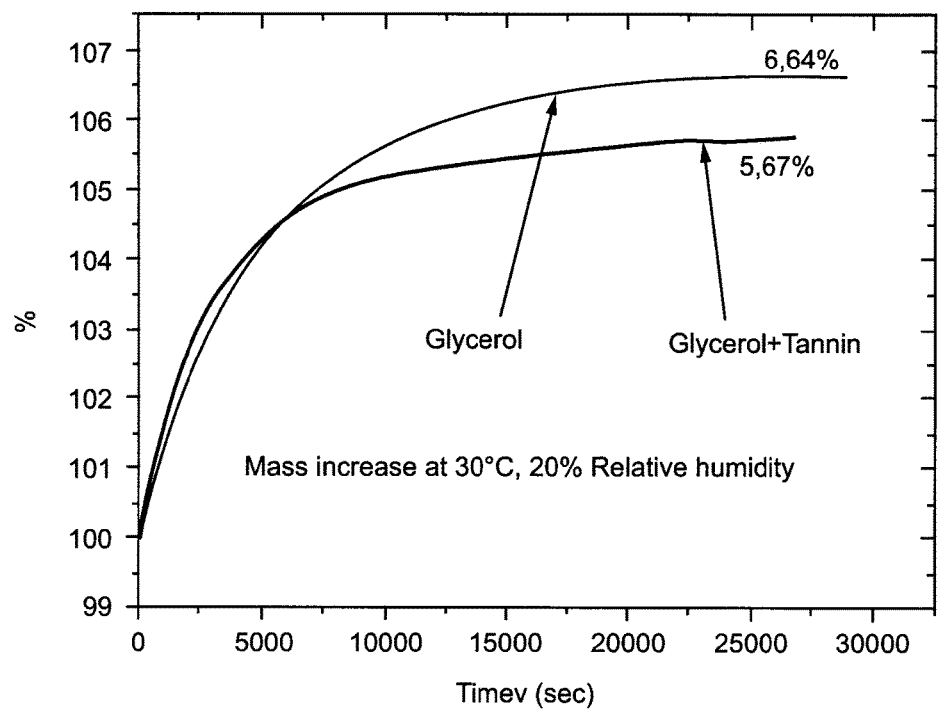

This application is a Continuation application of pending U.S. patent application Ser. No. 14/896,006 titled "COMPOSITION FOR TOPICAL APPLICATION COMPRISING GLYCEROL AND TANNINS" filed Dec. 4, 2015, which is the 35 U.S.C. § 371 national stage application of PCT Application No. PCT/EP2013/061835 titled "COMPOSITION FOR TOPICAL APPLICATION COMPRISING GLYCEROL AND TANNINS" filed Jun. 7, 2013, the entire disclosures of which are incorporated herein by reference.

BACKGROUND

Almost all the skin and mucosa injuries, whether of bacterial, viral, immunological or traumatic origin, involve cellular damage, and their healing is directly related to the replacement of damaged cells. In order to grow, cells need a hydrated and clean, pathogen-free, chemical-free, waste protein- and proteolytic enzyme-free environment. Under these conditions, the mother cells secrete a cellular matrix composed of free particles of collagen, elastin, laminin, fibronectin and other proteins, which form a cushion for the attachment of daughter cells. In absence of this matrix, daughter cells have no support to attach onto and therefore cannot grow; consequently, the injury cannot heal.

Topical skin and mucosa injuries involving cellular damage are extremely difficult to heal as, in addition to containing dead cells, cell debris, and multiple proteolytic enzymes which impede cell growth and wound repair, those lesions remain open to the external environment and often get contaminated. This is the reason why most chronic wounds such as bedsores, diabetic ulcers, or venous leg ulcers, never heal, and nearly 40% patients die before they experience wound resolution.

Currently, there is no single substance or product having all the multiple and essential properties needed, and there is no complete treatment available for skin and mucosa injuries. For example, there is presently no treatment for healing chronic wounds. All the drugs available either act as antiseptics, antibiotics to reduce microbial growth, as hydrogels or alginates to keep the wound hydrated, as analgesics or anesthetics to reduce the pain, as collagen- or hyaluronic acid-containing preparations to supply one of the cellular matrix' components, or consist of bioengineered skin or epidermal grafts to replace the skin, but none of these treatments is directed to clean the injury and to favor the natural skin or mucosa repair process by promoting cell growth.

The same lack of efficient treatment is true for topical viral infections such as labial herpes, genital herpes, rhinosinusitis, and influenza, where huge amounts of free virus particles are present on the infected biological surface and continue attacking new healthy cells with the help of topically available proteases. A virus infection is often mediated through multiple proteases present on the surface of the injury. Presently, there is no drug to reduce the amount of free virus particles or of proteases, the main agents of infection. To treat viral throat infection, sea water or salt water gargarism is still considered one of the best remedies as these osmotically active solutions form a hypertonic film over the throat mucosa and the resulting outward exudation of hypotonic liquid helps reduce the contaminant load on the throat surface. Unfortunately, this hypertonic solution film gets diluted within a few minutes by the outflowing hypotonic liquid, limiting the efficacy of that treatment. Increasing the concentration of salt or other osmotic ingredients is not recommended because of the resulting strong irritation, cellular damage and mucosa burning, or because the presence of a toxic chemical in the vicinity of cells would block cell growth.

Therefore, it is highly important to find a substance capable of fulfilling the multiple requirements of cleaning the infected surface of all the contaminants, such as free-floating bacteria, virus particles, dead cells, cell debris, dead proteins, matrix metalloproteases, growth factors, cytokines, proteases, or dust particles, so as to provide the environment essential for cell growth and tissue repair, without any toxic effect on the cells or the cellular matrix.

Glycerol, a polyol with multiple hydroxyl groups, is a viscous, transparent, safe, osmotically active, hydrophilic solution of natural or synthetic origin. Glycerol is commonly used as a food ingredient, preservative, and humectant, and enters into the composition of many cosmetics and pharmaceuticals. Glycerol is widely employed for topical application on wounds and burns, often as an excipient in association with other active ingredients. In all these preparations, glycerol is used as vehicle, diluent, viscosity enhancer, humidifier, or taste modulator but not as an active ingredient to treat a topical skin or mucosa pathology.

An injured skin or mucosa acts as a semi-permeable membrane and allows osmosis to occur. The flow of solvents across a semi-permeable membrane constitutes the osmotic flow or osmosis. The pressure required to achieve osmotic equilibrium is known as osmotic pressure. The higher the concentration of a solvent, the more osmotic pressure it exerts. Fresh water is considered isotonic with a density of 1000 kg/m$^3$. Seawater and glycerol have densities of 1025 kg/m$^3$ and 1259 kg/m$^3$, respectively. Osmotic pressure exerted by glycerol is nearly 10 times higher compared to seawater. The solute concentration of glycerol is also much higher compared to seawater. It is the total solute concentration in a solution that determines the osmotic flow of liquid, as osmosis is driven by differences in solute/solvent concentrations that exist across a semi-permeable membrane. The total solute concentration can be determined through the osmolality of the solution. The osmolality of seawater, containing 3.4% NaCl, is 0.581 mols/kg (total solute/mol wt/kg), compared to 10.86 mols/kg for glycerol. This shows that pure glycerol is nearly 18 times more osmotically active than seawater. Therefore, glycerol could have been a product of choice for application on infected surfaces in order to generate osmotic outflow of hypotonic liquid and to clean the injury. Unfortunately, the exudating hypotonic liquid immediately dilutes the glycerol and drains it from the wound surface within a few minutes, limiting these cleaning effects.

There is therefore a need for a safe and non-irritant treatment with the multiple properties of being hydrating, cleaning, antiseptic, and also having antibacterial, antiviral, and anti-protease activity.

WO 00/74668 discloses the use of hypertonic osmotically active solutions for the treatment of topical injuries concerning the use of glycerol as viscous solution for topical application for the treatment of ulcers or superficial injuries, comprising glycerol as active principle and a hydro-glycerinated extract of *Alchemilla vulgaris* as cell growth-promoting agent. However, the glycerol used in WO 00/74668 is not filmogen and therefore cannot provide for the above detailed advantages. The use of glycerol alone as a therapeutic agent to clean infected or damaged tissue is not common because, due to osmosis, the phenomenon of hypotonic liquid outflow from the inner parts of the tissue, glycerol gets diluted within a few minutes, progressively loses its osmotic properties and activity, and does not satisfactorily act as a total cleaning agent. The glycerol film should remain on the semi-permeable live tissue membrane for at least 30 minutes to generate sufficient osmosis to clean the biological tissue surface.

The present invention deals with the problem of how to improve the retention time of the glycerol film by a live biological surface in order to overcome the above-mentioned disadvantages.

Secondly, Cryopreservation is a process where cells, whole tissues, or any other substances susceptible to sustain damage caused by chemical reactivity or time, are preserved by cooling to subzero temperatures. At low enough temperatures, any enzymatic or chemical activity, which might cause damage to the material in question, is effectively stopped. Cryopreservation methods seek to reach low temperatures without engendering additional damage caused by the formation of ice crystals during freezing. For long term live cell storage, the cryoprotectant must be non-toxic to the cells and be able to prevent crystal formation. This is particularly important for live cell and tissue storage or preservation (example: skin graft) since the chances of successful cell revival or tissue grafting diminish as the number of dead or dying cells increases.

Currently, DMSO (Di-Methyl-Sulfoxide), human or fetal calf serum (FCS), and glycerol are used as cryoprotective medium to protect the cells against freezing temperatures and water crystal damage, and thus minimize cell mortality. Unfortunately, none of these cryopreservants is capable of preserving the cells over a long period of time, i.e. a few months to a few years. Normally, 30-40% cells die within a few days and over 50% within a few months of live cell cryopreservation (Bravo et al. Burns 26(4), 367-78, 2000), due particularly to cellular damage caused by the formation of water crystals.

There is therefore an urgent need to find a cryopreservant which is capable of forming a thin film around the cells or the tissue and protect them from external aggressions as well as from the formation of water crystals in order to enhance cell viability.

SUMMARY

To solve the above detailed problems, the inventors provide a glycerol preparation containing specific plant tannins capable of binding to glycerol molecules and thereby improving the filmogenic properties and retention time period of the glycerol preparation on semi-permeable biological membranes. This filmogen glycerol can be used as a natural and safe treatment for topical application, to treat various skin and mucosa infections and to protect live tissues during cryopreservation.

Present invention therefore deals with a preparation for topical application comprising glycerol and plant tannins. The plant tannins have the capacity to bind to glycerol so that the glycerol has filmogen qualities.

In one embodiment, the plant tannins are chosen from proanthocyanidins.

In a preferred embodiment, these proanthocyanidins are obtained from parts of a plant, or the whole plant, the plant being selected from *Vaccinium myrtillus, Vaccinium macrocarpon, Vitis vinifera, European elder, Camellia sinensis, Glycine max, Acacia catechu, Fraxinus chinensis, Gingko biloba, Ribes nigrum, Tenacetum parthenium, Salix alba, Salvia officinalis, Rosmarinus officinalis, Opunitia* sp., *Morus alba, Rubus* sp., *Quercus* sp., *Pinus* sp., and combinations thereof.

In a more preferred embodiment, the proanthocyanidin-rich tannin fraction is obtained from parts of a plant, or the whole plant, the plant being selected from *Vaccinium myrtillus, Vaccinium macrocarpon, Vitis vinifera, European elder, Camellia sinensis, Ribes nigrum, Acacia catechu, Fraxinus chinensis, Gingko biloba, Glycine max*, and combinations thereof.

In another embodiment, the proanthocyanidins are synthesized instead of being obtained from plants.

In one embodiment the glycerol content in the preparation is comprised between 30% and 99.99% (v/v).

In one embodiment, the preparation comprises an active ingredient. The active ingredient can be selected from a drug, an antibiotic, an antiseptic, a nutrient, an antibody, a growth factor or a protein.

Present invention furthermore deals with the use of the above-described preparation for the treatment of skin and mucosa infections.

The above-described preparation can further be used for protecting, transporting, storing or freezing cells, tissues or organs. In one embodiment the concentration of filmogen glycerol in the final solution compared to other diluents present in the final solution, such as for example FCS, culture medium, and DMSO, varies between 2 and 50% (v/v), preferably between 10 and 30% (v/v) and more preferably between 15 and 20% (v/v).

Present invention also relates to a method of enhancing the retention time of a glycerol film by a biological surface by preparing a solution of glycerol and plant tannins having the capacity to bind to glycerol molecules, and applying the solution onto the biological surface.

Present invention also relates to a method of treating skin and mucosa infections comprising the step of applying a preparation as described above on the affected area.

Present invention also relates to a method of preparing filmogen glycerol comprising mixing glycerol or a polyol solution with glycerol-binding plant tannins. In one embodiment the plant tannins can be added as a powder or a liquid.

The amelioration of filmogen qualities of glycerol with the addition of tannins and a substantial increase in the therapeutic efficacy of filmogen compared to non-filmogen glycerol, are shown in the studies as described in the examples and in the following figures:

FIGURES

FIG. 1: Measurement of solubility of glycerol alone compared to filmogen glycerol through thermogravimetric analysis (TGA).

Figure 2:
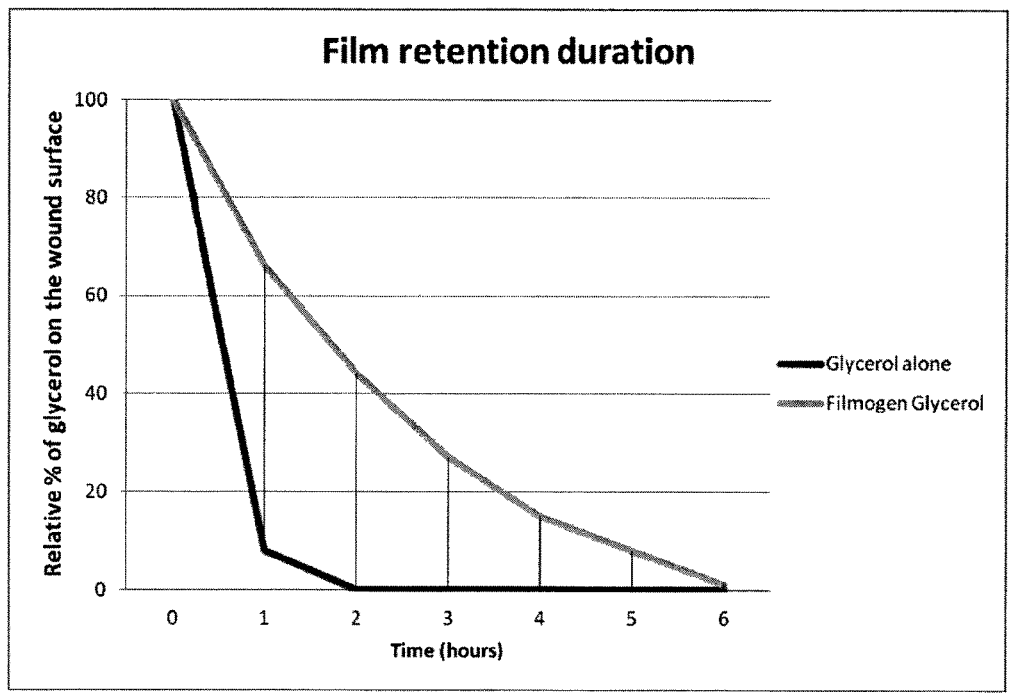

FIG. 2: Film retention duration of filmogen glycerol compared to normal glycerol on diabetic wounds.

Figure 3:
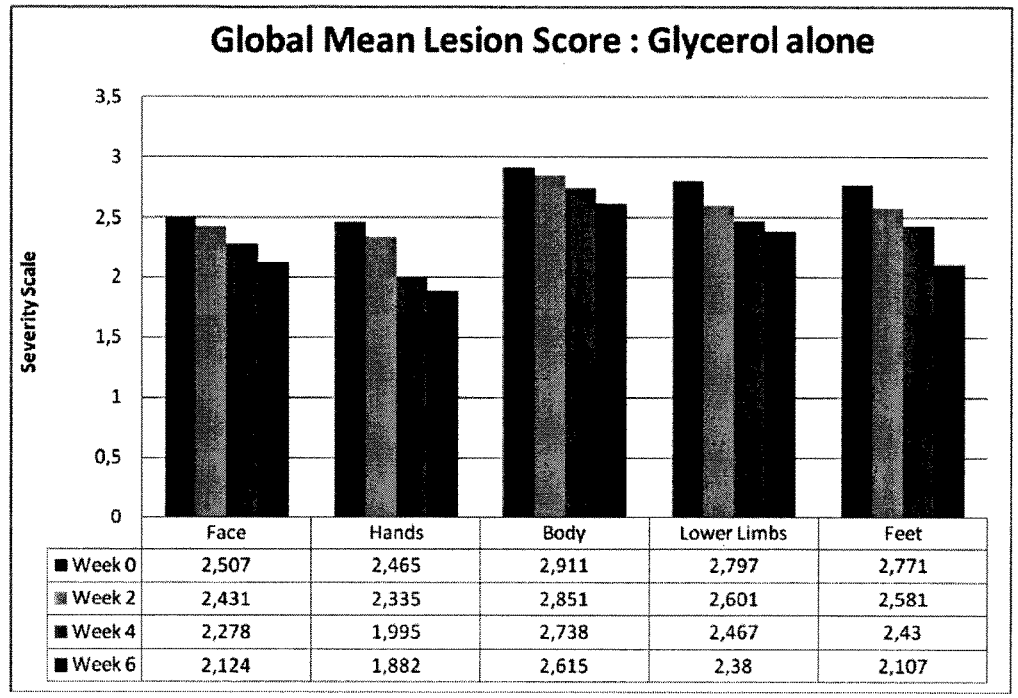

FIG. 3: Measurement of mean global symptom severity of Psoriasis, Eczema & Dermatitis (PED) manifestations: Effects of Glycerol alone—Control Group.

Figure 4:
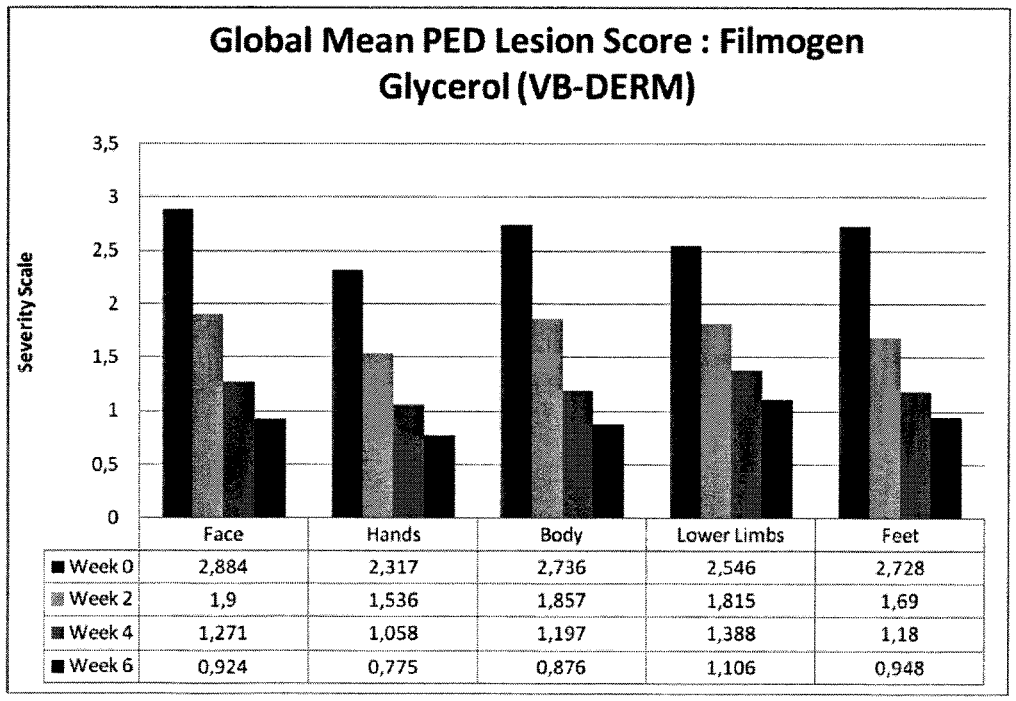

FIG. 4: Measurement of mean global symptom severity of Psoriasis, Eczema & Dermatitis (PED) manifestations: Effects of filmogen glycerol; Active Treatment Group: treated with filmogen glycerol VB-DERM as per Example 5 preparation n° 11, and 51. Results show that filmogen glycerol totally removes all the free particles of growth-stimulating cytokines, interleukines, and interferons, and normalizes skin cell growth.

Figure 5:
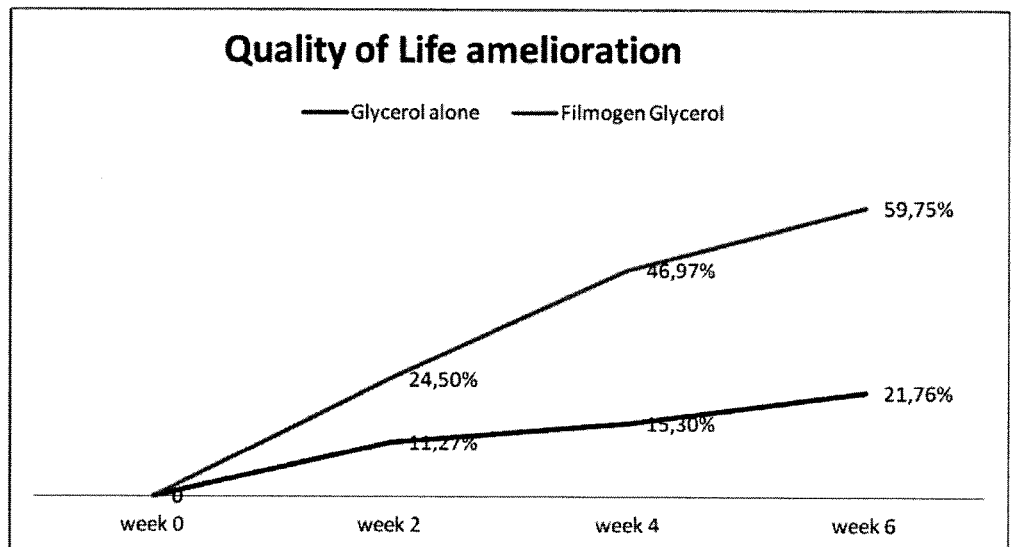

FIG. 5: Amelioration in the quality of life of PED patients treated with Filmogen Glycerol compared to normal Glycerol.

Figure 6:
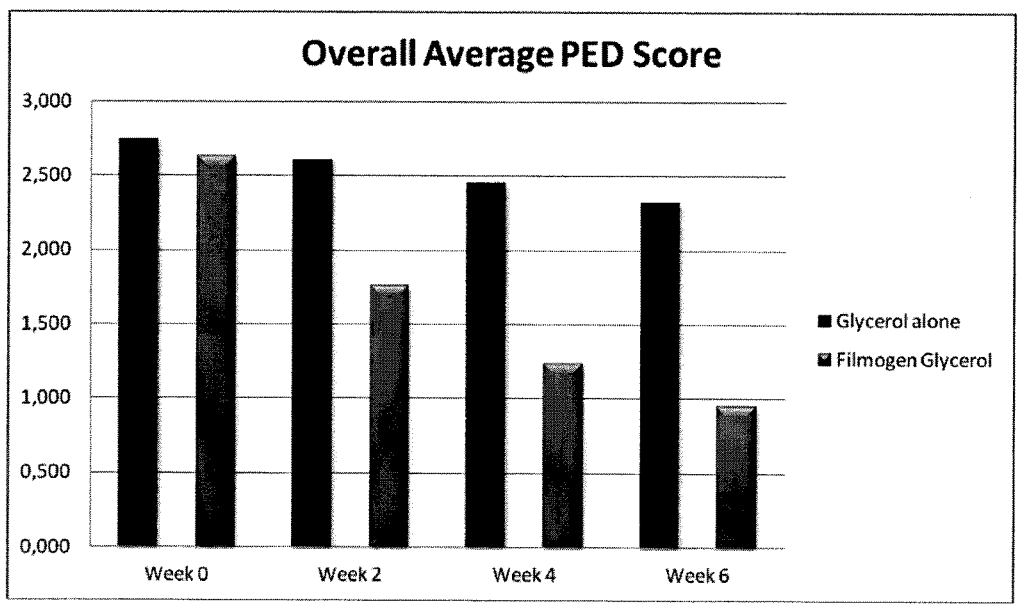

FIG. 6: Effects of respective treatments (Filmogen Glycerol compared to normal Glycerol) on Overall PED Severity.

Figure 7:
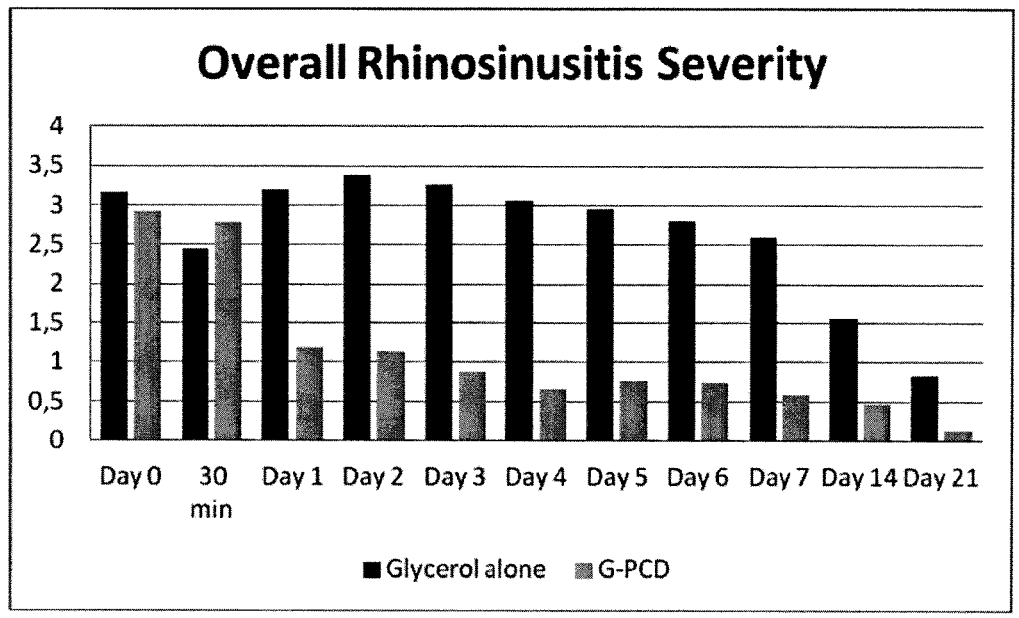

FIG. 7: Overall rhinosinusitis condition; control group treated with normal glycerol spray; filmogen glycerol group treated with a spray of filmogen glycerol as per example 5—preparation n° 5.

Figure 8:
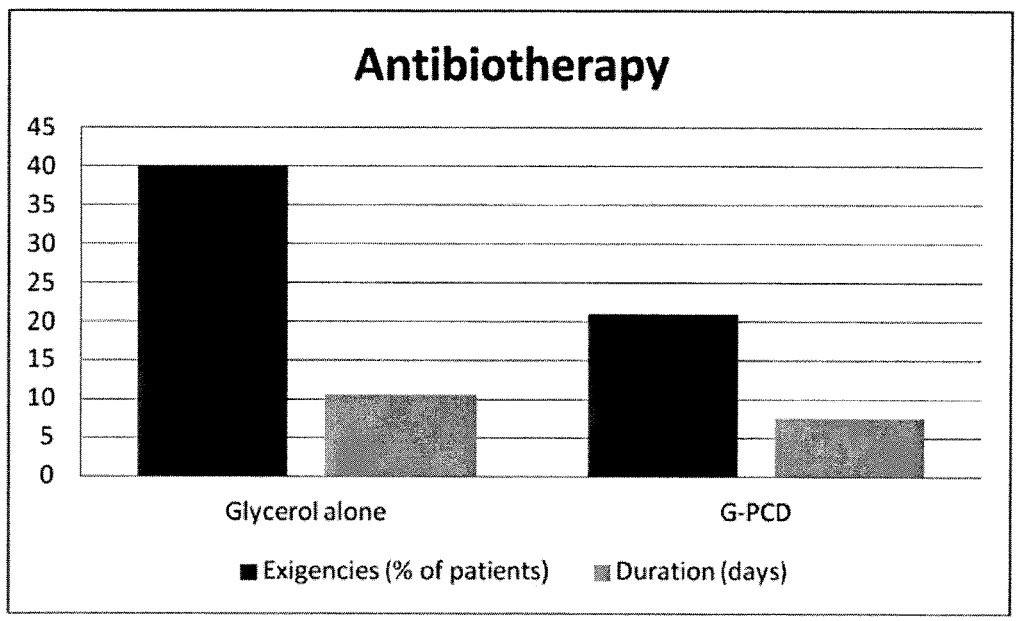

FIG. 8: Antibiotherapy; the comparative necessity to use antibiotic treatment in the control group and the filmogen glycerol group.

Figure 9:
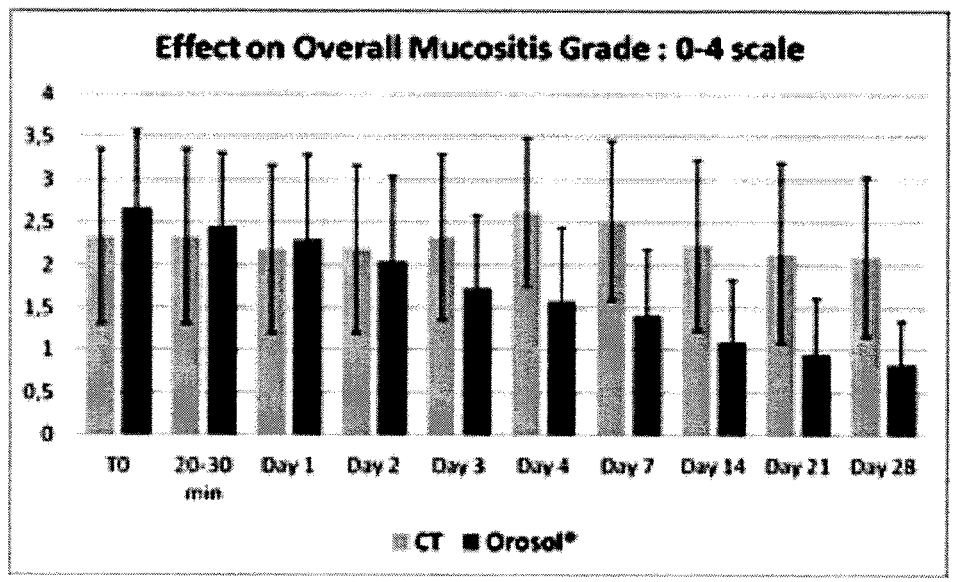

FIG. 9: Effects of Orosol (filmogen glycerol) compared to control treatment (glycerol alone) on Mucositis.

DETAILED DESCRIPTION

Present invention deals with a filmogen glycerol preparation for topical application comprising glycerol and plant tannins. The plant tannins have the capacity to bind to glycerol so that the glycerol has filmogenic properties. This filmogen quality leads to an enhancement of the retention time of the glycerol film by a live biological surface. As such the preparation is intended for use for the treatment of skin and mucosa infections.

The term filmogen glycerol indicates a glycerol solution containing specific, natural or synthetic tannins or fractions of tannins, which, when applied on a semi-permeable live biological membrane, forms a film which resists the mechanical forces exerted on it much better than normal glycerol would. When normal, commercially available, glycerol is applied on a semi-permeable biological membrane, the hypertonic nature of glycerol attracts hypotonic liquid from the inner parts of the live tissue, which causes the glycerol to get rapidly diluted, lose osmotic power and stop its activity within 10-15 minutes after application. On the other hand, a filmogen glycerol resists the outward liquid flow pressure exerted on it, and gets diluted only slowly, therefore conserving its osmotic power for a much longer period of time than normal glycerol, i.e. 30 minutes to a few hours depending upon the site of application and the outward liquid flow pressure.

Glycerol, also known as glycerine or glycerin, includes per definition sugar alcohol compounds containing more than one hydroxyl group (OH), attached to separate carbon atoms of an aliphatic skeleton. This group includes glycols, glycerol, and pentaerythritol and also such products as trimethylolethane, trimethylolpropane, 1,2,6-hexanetriol, sorbitol, inositol, Xylitol, and poly(vinyl alcohol). Polyols may be obtained from natural sources or can be synthesized.

We selected the most commonly used polyol i.e. glycerol. Glycerol is a hypertonic viscous sugar alcohol solution, which attracts hypotonic liquid present in the deeper tissues underlying the live biological surface through osmosis, thereby hydrating that surface. Unfortunately, the outward hypotonic liquid flow thus generated dilutes glycerol and progressively diminishes this effect within a few minutes. The outward exudation of hypotonic liquid and consequently the cleaning effects of glycerol only last for a period of 5 to 20 minutes, requiring frequent applications, which is not practical. This is the reason why, despite being a good osmotic agent, glycerol is used only as a humectant and not as a proper drug for the treatment of topical injuries.

Filmogen glycerol signifies a viscous liquid glycerol which forms a thin osmotically active, semi-permeable, flexible, non-plasticizer film capable of attracting hypotonic liquid from the live biological surfaces onto which it is applied and capable of better resisting disintegration or water solubility compared to standard glycerol.

Tannins comprise natural astringent polyphenolic compounds containing sufficient hydroxyl and other suitable groups such as carboxyls to form strong complexes with proteins and various other macromolecules such as sugars.

Tannins may be of natural origin, such as plant tannins, or synthetic. Being highly branched and large molecules, monomer, dimer and polymer tannins have more chances of binding with adjacent sugars or other molecules compared to small and simple flavones. The presence of hydroxyl groups on tannins permits the formation of stable cross-links with macromolecules such as polyols, and this crosslinking helps improve the mechanical resistance of the polyol (glycerol) film. Because of the multiple toxic effects of synthetic polymers cited in the literature, the inventors postulated that vegetal tannins, having a strong affinity for binding with proteins but equally with other macromolecules such as polysaccharides, carbohydrates and sugars, may, when added to the polyols, improve the filmogenic properties of the polyol, e.g. glycerol. Tannins constitute an excellent solution as: (1) tannins are inert molecules and have no interactions with cellular structures; (2) tannins are non-toxic and non-irritant when applied onto a live tissue; (3) tannins are very big molecules and cannot enter the cells; and (4) tannins can be incorporated into glycerol to form a homogenous solution.

Generally, tannins are classified into two broad groups: hydrolysable and condensed tannins. As the name indicates, hydrolysable tannins are quickly hydrolyzed by acids or enzymes, and the products of this hydrolysis are gallic acid or ellagic acid. Upon dry distillation, gallic acid and other components get converted to pyrogallol. Condensed tannins are much more resistant to hydrolysis. They are formed by flavonoid pigments. In presence of mineral acids or enzymes, they are decomposed into red colored phlobaphenes that are water insoluble. Proanthocyanidins (PCDs) are condensed phenolic polymers containing flavan-3-ol units linked together through C4-C6 or C4-C8 bonds. Structural variation of proanthocyanidins ranges from dimers and trimers to more complex oligomers and polymers depending on the number of catechin linkages, hydroxylation and stereochemistry at the three chiral centers (carbon 2, 3 and 4) of the C-ring which is not susceptible to cleavage by hydrolysis. The inventors have observed that the procyanidins (PCDs) formed from 2 to 5 catechin or epicatechin molecules are especially well suited for macromolecular binding.

In one embodiment of present invention the plant tannins are chosen from proanthocyanidins or procyanidins (PCDs).

In a preferred embodiment these proanthocyanidins are obtained from parts of a plant, or the whole plant, the plant being selected from *Vaccinium myrtillus, Vaccinium macrocarpon, Vitis vinifera*, European elder, *Camellia sinensis, Glycine max, Acacia catechu, Fraxinus chinensis, Gingko biloba, Ribes nigrum, Tenacetum parthenium, Salix alba, Salvia officinalis, Rosmarinus officinalis, Opunitia* sp., *Morus alba, Rubus* sp., *Quercus* sp., *Pinus* sp., *Rheum emodi* and combinations thereof.

In another embodiment the proanthocyanidins are synthesized instead of being obtained from plants.

The inventors have found out in the wake of their studies (see example 3—Pharmacological studies) that certain PCDs or their combinations) are very highly filmogenic, meaning that they increase the glycerol film retention duration between 200 and 300% compared to glycerol alone. These combinations preferably consist of: *Vaccinium myr-*

*tillus* (fruit extract)+*Vaccinium macrocarpon* (fruit extract); *Vitis vinifera* (seed extract)+*European elder* (fruit extract); *Camellia sinensis* (leaf extract)+*V. myrtillus; V. myrtillus+E. elder; C. sinensis+V. vinifera+E. elder; V. Vinifera+E. elder+Glycine max* (seed extract); *V. macrocarpon+C. sinensis+V. vinifera*; and *V. macrocarpon+C. sinensis+V. myrtillus+V. vinifera*.

In comparison to that, the following tannin-rich plant extracts combinations have been found to have high filmogenic qualities, meaning that they increase the film retention duration between 100 and 200% compared to glycerol alone: *Acacia catechu+Fraxinus chinensis* (bark and whole plant); *F. chinensis+Salvia officinalis+G. biloba; Rosmarinus officinalis+Ribes nigrum; Gingko biloba* (roots)+Synthetic polymers.

In addition, another group has been specified as having moderately filmogenic qualities, meaning that they increase the film retention duration between 20 and 99% compared to glycerol alone: *Morus alba* (fruits)+*Rubus* sp. (fruits); *Quercus* sp. (fruits, bark)+*Pinus* sp. (bark, fruit). *Tenacetum parthenium* (flowers and leaves)+*Salix alba* (whole plant); *Rheum emodi+Opunitia* Sp. (fruits)+*Pinus* sp (bark).

These combinations are interchangeable.

It is well known that polyols and polymers contain sufficient free oxygen molecules to form strong hydrogen bonds with the hydroxyl group of the phenolic compounds. Many studies have been conducted with synthetic or natural, water soluble or water insoluble, purified or crude, polymers to investigate the bioavailability and digestibility of plant tannins, to prepare synthetic polymers and plastics, to improve the viscosity or rigidity of materials or to quantify tannins, but the use of tannins or polymers to improve the filmogenic properties of glycerol for topical application to treat skin or mucosa injuries has never been studied.

It is to be understood that present invention does not concern the use of glycerol as plasticizer or the use of glycerol as humectant on the skin. The addition of tannins in glycerol does not change the viscosity of glycerol or of the glycerol film on the biological membrane but enhances the adherence of glycerol onto the live biological membrane.

The aim of the research conducted by the inventors was to identify plant tannins, particularly the procyanidin (PCDs) fraction of plant tannins, which can bind with glycerol molecules to form a mechanically resistant glycerol film able to remain intact over the biological membrane during the exudation of hypotonic liquid. The purpose being to implement this optimally bio-adhesive, osmotically active, hypertonic and safe film as an effective treatment to clean injuries, remove contaminants from the injury, keep the injury hydrated, protect the cellular matrix and prepare a favorable ground for cell growth in a non-toxic, chemical-free environment.

The inventors identified specific glycerol-binding plant tannins capable of improving the mechanical resistance of the glycerol film and thereby keeping the film intact over live cells for a much longer period of time compared to glycerol alone. This increased duration of retention of the filmogen glycerol over a damaged skin or mucosal surface effectively hydrates and cleans the biological surface as well as removes all the free-floating contaminants present on the surface. The absence of contaminants and a clean and humid environment accelerate the healing of the injured tissue. Glycerol film equally protects the injured surface from external aggressions.

Glycerol is also used as a cryoprotectant while freezing cells and tissues at low temperatures (−70 to −196° C.). The hydroxyl groups of glycerol interact with $H_2O$ and block the crystal-forming properties of water. The molecular organization of $H_2O$ is modified, leading to less water crystal formation during freezing and low cellular damage. Glycerol is generally used up to a concentration between 5 and 20% along with DMSO (1-5%), serum (10-20%) and culture medium for freezing cells and live tissues. DMSO makes the cell membrane porous, which protects the cells from damage during thawing while glycerol protects the membrane structures and maintains the nature of internal proteins. Above a concentration of 20%, glycerol becomes too hypertonic and damages the cell due to its osmotic effects. Unfortunately, cell survival with these cryoprotectants rarely exceeds 60%, leading to poor grafting of the stored tissues. Higher concentrations of any of these ingredients were not found to enhance cell survival. The poor cell survival rate is due to the fact that in spite of high concentrations of glycerol molecules present around the live cell membranes, cellular dehydration during freezing liberates a large number of $H_2O$ molecules on the membrane surface. This water is trapped by glycerol but as the glycerol is not present as a film, some water molecules crystallize. Water crystals further increase the distance between free glycerol molecules and the cell membrane, which fosters further water crystal formation and subsequent cellular damage. Even after considerable efforts to find a filmogen cryoprotectant capable of protecting the complete cell surface and trapping all the water molecules diffusing from inside the cell, no safe filmogen cryoprotectant has yet been discovered.

It has been found by the inventors that a filmogen glycerol remaining in close contact with the cell membranes can better preserve the live cells compared to glycerol alone. The above-described preparation can thus further be used for protecting, transporting, storing or freezing cells, tissues or organs. In one embodiment the net concentration of filmogen glycerol in the sample varies between 2 and 50% (v/v), preferably between 10 and 30% (v/v) and particularly between 15 and 20% (v/v). Filmogen glycerol therefore constitutes an excellent solution to overcome this difficulty and to prevent water crystal damage to the cells.

In one embodiment of present invention the glycerol content in the preparation is comprised between 30% and 99.99% (v/v). The % of glycerol in the preparation for topical application may vary according to the part of the body where product is applied, for example a thicker product for application on open chronic wounds, a less thick product for application in the vaginal cavity or a much thinner preparation for application in the nasal or oral cavity. The percentage of glycerol in the preparation can vary between 30 and 99.99% (v/v), for example between 90 and 99% (v/v) for vaginal application, between 70 and 99.9% (v/v) for application on skin wounds, between 30 and 60% (v/v) for application on sensitive mucosa such as the nasal mucosa.

In another embodiment the preparation further comprises an active ingredient. The active ingredient can be selected from a drug, an antibiotic, an antiseptic, a nutrient, an antibody, a protein, a growth factor, or any other substance requiring being in contact with the injured surface onto which the glycerol film is applied.

The preparation can be filled into tubes, plastic containers, syringes, ampoules, sprays, metallic containers, in volumes between 1 and 500 ml depending upon the type of containers. Filmogen glycerol can also be incorporated in cotton, polymer, plastic, cellulose or other type of dressings commonly used for application on the wounds and injuries.

Present invention also relates to a method of enhancing the retention time of a glycerol film by a biological surface by preparing a solution of glycerol and plant tannins having the capacity to bind to glycerol molecules, and applying the solution onto the biological surface.

The concentration of tannin-rich plant extracts in glycerol may vary depending upon the initial concentration and composition of the tannins used to obtain the filmogen effect.

The inventors have made the following hypothesis regarding the working mechanism of the preparation. An osmotically active solution can be applied on biological surfaces where cell plasma membranes are exposed to the external environment (skin injuries where skin keratinocytes are damaged and the underlying cells are exposed, mucous membranes such as the throat, and the oral, nasal and vaginal cavities) so as to form an osmotically active film over the biological membrane and create an outward flow of hypotonic liquid. The outward flow of liquid should detach and drain impurities such as dead cells, cell membranes, dust particles, bacteria, virus particles, free-floating protein molecules such as proteases, etc . . . , resulting in the cleaning of the injury and mucous membrane. This mechanical mode of action produces antibacterial, anti-viral, antiseptic, cleaning and hydrating effects, which are essential to promote cell growth and healing. Sea water, containing 3-3.4% NaCl (salt), is commonly used to clean injuries or for gargling, but is not very effective because the outward flow of hypotonic liquid instantly dilutes and removes the osmotic film, limiting the duration of action of the saline solution to only a few minutes. The shorter the duration of retention of hypertonic film by the biological surface, the lesser its cleaning efficacy.

Glycerol is much more viscous than seawater or a 3% saline solution and remains over the biological membrane for a relatively longer period than seawater. As glycerol is a non-toxic, non-irritant, totally safe, and inexpensive product for topical application as an antiseptic, antiviral, cleaning and hydrating agent, it should have been widely used to treat topical infections, clean wounds and promote wound healing. But this is not the case because glycerol is also diluted by the outward flow of hypotonic liquid it generates through its very osmotic activity, and is consequently removed from the surface only a few minutes after its application, which considerably shortens the duration of glycerol's action, and does not allow sufficient time for thorough surface cleaning. This explains why the use of glycerol alone for cleaning mucous or injured surfaces is not satisfactory.

The three hydroxyl groups of glycerol render it easily soluble in water through the formation of hydrogen bonds with water. Diluted glycerol is immediately eliminated with the hypotonic liquid flow, which progressively but rapidly (within 5-10 minutes) diminishes the osmotic effect of glycerol. The only solution to overcome this problem would be to keep reapplying the product repeatedly, every 10-15 minutes, to reconstitute the osmotically active film, which is not practical.

Therefore, the best solution involves improving the film retention duration of glycerol without altering the osmotic properties or the safety profile of the product, so as to provide an effective, safe, and inexpensive method for cleaning biological surfaces.

As glycerol acts on the biological surface exclusively through its mechanical properties, without any biological, pharmacological, metabolic or immunological interaction with the underlying live biological membranes or cells, it is important that the substance that is chosen for its capacity to improve the filmogenic properties of glycerol be similar or inert.

Present invention also relates to a method of treating skin and mucosa infections comprising the step of applying a preparation as described above on the affected area. In present application the term skin refers to skin of all areas of the body, also including, for example, the very sensitive skin on the lips. The present preparation can equally be applied onto the skin and the mucous membranes such as the oral cavity, throat, nostrils, nasal sinuses, damaged skin and tissues on the surface of the body, vaginal cavity and other natural openings of the body. Skin and mucosa infections signify the presence of any undesirable pathogen or material on the surface of the skin or mucosa, interfering with normal cell functions or with the healing process.

Present invention also relates to a method of preparing filmogen glycerol comprising mixing glycerol or a polyol solution with glycerol-binding plant tannins. In one embodiment the plant tannins can be added as a powder or a liquid.

Present invention is furthermore illustrated by, but not limited to the content of, the following examples.

EXAMPLES

Example 1: Preparation of Tannin-Rich Plant Extracts

Initially, 186 tannin-rich plant substances were selected for the preparation of proanthocyanidin (PCD)-rich, dry plant extracts.

The PCD-rich plant extracts were prepared from different plant materials rich in tannins such as fruits, seeds, skins, flesh of vegetables, nuts, tree barks, and any other tannin-rich plant material. The raw material was used either as is (wet) but might also have been presorted by drying, separating and removing the components low in tannins.

Tannin-rich plant extracts were prepared using standard methods described in the literature (Ajila CM. Crit Rev Biotechno, 31 (3) 227-249, 2011) and known to the man of art. In short, during the initial phase, an aqueous mixture of solid plant material containing proanthocyanidins was prepared by heating approximately 4 kg of solid plant material with 24-40 liters of deionized water (ratio of solid material to water being 1:6 to 1:10), optionally under increased pressure (60-100 psi pressure) and at a temperature between 180 & 250° C., for a period ranging between 30 minutes and 5 hours, depending upon the rigidity of the plant material processed. After heating, the liquid extract was separated from larger debris by passing the mixture through a cotton bandage cloth. The separated solids were discarded and the PCD-rich liquid was collected. The extract was then dried by heating (180-200° C.) or by atomization and used as PCD-rich extract for various experiments as well as for incorporation into glycerol.

The proanthocyanidin content in the extract was determined by the Acid Butanol assay according to the method of Porter et al. (Porter et al. Phytochemistry, 1986). In short, 200 µg dried plant extract was diluted with 300 µl of 70% acetone and the solution was pipetted into a 100×12 mm test tube. 3.0 ml of butanol-HCL reagent (95:5) and 0.1 ml of 2% ferric acid prepared in HCl 2N were added. The tube was vortexed and then the mouth of the tube was covered with a glass marble and put in the heating block at 97 to 100° C. for 60 minutes. The tube was then allowed to cool down, and absorbance was recorded at 550 nm. The formula for calculating the percentage of condensed tannins as leucoanthocyanidin equivalent is: (absorbance 550 nm×78.26×dilution factor)/(% dry matter).

Only those plant extracts (42 out of the 186 tested) having a Porter value above 200 and indicating a high concentration of PCDs were used for further testing. The extracts were not purified to concentrate a specific type of tannin as best results were obtained with a mixture of PCDs and not with a particular type of tannin. Dried plant extracts mainly contain dimers, trimers and pentamers catechin building blocks.

Example 2: Preparation of Filmogen Glycerol

According to the type of glycerol film required for topical application, 0.1 to 8.0% PCD-containing dry powder was incorporated into glycerol and thoroughly mixed for 6 h at 37° C. under agitation to obtain a homogenous solution. Glycerol of vegetable origin can be purchased from suppliers such as Interchimie in France. The preparation was filled into tubes, plastic containers, syringes, ampoules, sprays, metallic containers, in volumes between 1 and 500 ml depending upon the type of containers and the desired use.

Example 3(a): Pharmacological Studies: Measurement of Film Retention Capacity of Glycerol Alone Compared to Glycerol Containing Different Plant Tannins Experiments were conducted to study the effects of a new glycerol film containing PCD-rich plant extracts (filmogen glycerol) as compared to a non-PCD glycerol film (normal glycerol) under identical conditions. The aim of this study was to select those individual PCDs, or their associations, which improve the retention of glycerol film by the biological membrane.

Test Model:

In the absence of any specific in vivo model to study the duration of the film retention by a biological surface, an in vitro model of human multilayered epidermis was used to evaluate the effects of the addition of non-cytotoxic concentrations of different PCD-rich plant extracts, either singly or in different associations, on glycerol film retention. Human epidermis was grown on a permeable polycarbonate filter (1 cm diameter) and was kept on a sponge soaked with culture medium, its outer surface remaining in contact with air, as is the case in vivo. Through capillary action, the culture medium diffuses through the polycarbonate filter and supplies nourishment to the epidermal cells to keep those cells alive.

Inserting one or two additional polycarbonate filters increases the distance between the culture medium and the cells; the amount of available medium, which reaches the cells, then decreases, and in absence of nutrients and hydration, the cells die. Cell death can be measured by vital MTT staining (Ferrari M J. J Immunol methods 13 (2), 165-172, 1990). The percentage of live cells is proportional to the duration of retention of the glycerol film by the epidermal surface.

Test Products:

Various glycerol preparations containing test products (mainly PCD-rich plant extracts), at concentrations varying between 0.1 and 5.0%. Plant extracts were added to the film substance to study their effect on the film's cell-adhesive properties.

Quantity of Test Product Applied Per Epidermis: 20 µl

Method of Exposure:

Glycerol preparations were directly applied on the epidermis as thin layer with the help of a pipette (n=6 per concentration): the epidermis was placed on two filters and the test product was applied on the epidermis surface. The filters were kept on a sponge, which was inserted in a petri dish containing an appropriate quantity of medium to nourish the cells. During the experimental period, the cell culture filter was gently removed at 6 h, 24 h and 48 h, and stirred in a serum-free medium for a 20-second period to allow product film detachment (when the film or the film ingredients were not well adhered to the epidermal surface). Absence of osmotic film on the epidermis minimizes liquid culture medium supply to the cells and causes cell death. According to the initial results obtained for each test product concentration in glycerol, the concentration of plant tannins was either increased or decreased to obtain maximum filmogen effects.

Exposure Conditions:
37° C., 5% $CO_2$ for 72 hours.

Cell Viability Measurements:
MTT coloration and histological analyses. The cell viability was scored as follows:
Score 4: 100% cells (compared to the controls) with intense blue color.
3: Approximately 75% live cells with dark blue color.
2: Approximately 50% live cells with medium blue color.
1: Approximately 25% live cells with light blue color.
0: No live cells, whitish epidermis color.

During each experiment, the scores obtained for 6 epidermises at each time point were averaged to determine cell survival. The mean scores of 3 individual experiments were then averaged to calculate mean cell survival percentage as compared to cells treated with glycerol alone.

Controls:
Positive controls: No test product but the same test conditions as for the test products. Under these conditions nearly 95-100% cells die within 72 h.
Glycerol control: Identical to the positive controls with the exception that glycerol, free of any PCD extract, was applied on the culture surface. Under these conditions nearly 60-70% cells die within 72 h due to poor nutrient supply.

Results:
The cell survival % after 72 h was as follows:
Positive controls: 6.32 (±2.4)%
Glycerol alone: 23.85 (±4.8)% indicating 17.53% higher cell survival compared to the positive controls. This shows that glycerol exerts osmotic effects to continue nourishing and hydrating the cells.

Filmogen glycerol: When PCD-rich plant extracts or synthetic polymers were added to the glycerol at concentrations between 0.1 and 5.0%, cell survival was affected as follows:

Very high glycerol film retention capacity (+200 to +300% live cells compared to glycerol alone):
PCDs from: (1) *Vaccinium myrtillus* alone, and (2) association of PCD-rich plant tannins of *Vaccinium myrtillus* (fruit extract)+*Vaccinium macrocarpon* (fruit extract); *Vitis vinifera* (seed extract)+*European elder* (fruit extract); *Camellia sinensis* (leaf extract)+*V. myrtillus*; *V. myrtillus*+*E. elder*; *C. sinensis*+*V. vinifera*+*E. elder*; *V. Vinifera*+*E. elder*+*Glycine max* (seed extract); *V. macrocarpon*+*C. sinensis*+*V. vinifera*; and *V. macrocarpon*+*C. sinensis*+*V. myrtillus*+*V. vinifera*.

High film retention capacity (+100 to +199% live cells compared to glycerol alone):
PCDs from: (1) *Acacia catechu* (bark and whole plant), *Tenacetum parthenium* (flowers and leaves); *Salix alba* (whole plant); *Salvia officinalis; Rosmarinus officinalis; V. macrocarpon; V. vinifera; C. sinensis; E. elder; Opunitia* Sp. (fruits), singly, and (2) associations of *Fraxinus chinensis*+

Gingko biloba; Fraxinus chinensis+Gingko biloba+Camellia sinensis; V. vinifera+Ribes nigrum.

Moderate film retention capacity (+10 to +99% live cells compared to glycerol alone):

Morus alba (fruits); Rubus sp. (fruits); Quercus sp. (fruits, bark), Pinus sp. (bark, fruit).

Moderate filmogen activity was also obtained with synthetic polymers such as syntan containing polymers (example Blancotan SH2 and Ledosol CRP which can be purchased from Silvateam s.p.a., Italy) or polymeric resins (such as Aritan A7, an anionic nitrogen containing polymeric resin which can be purchased from Arihant Dyechem company in India).

Conclusion:

These results prove that many different tannins, but especially dimer to pentamer catechins, natural or synthetic, are capable of producing filmogen glycerol by binding with the glycerol molecules and are capable of improving the mechanical properties of the glycerol film over the biological surface.

In order to measure the filmogen quality of the preparations as prepared in example 2, tests were conducted, showing in an indirect manner that the filmogen quality of glycerol has been increased.

Example 3(b): Pharmacological Studies: Measurement of Solubility of Glycerol Alone Compared to Filmogen Glycerol In Vitro To verify the effect of the addition of tannins on glycerol's mechanical resistance to solubility in the water attracted through its own osmotic activity, we proceeded to thermogravimetric analysis (TGA) of glycerol alone versus filmogen glycerol (containing 1% tannin-rich plant extract). A film of the respective test substances was exposed to a constant temperature (30° C.) & relative humidity (20%) atmosphere and time-related mass increase was measured. Water solubility could thus be quantified (FIG. 1).

Preliminary results show that the tannin decreases glycerol's solubility in water. The reduced solubility is supposedly imputable to the tannin occupying some of glycerol's hydroxyl groups, which are therefore not available to bind with the water molecules.

Example 3(c): Pharmacological Studies: Measurement of Film Retention Duration of Glycerol Alone Compared to Filmogen Glycerol in Diabetic Ulcers Filmogen capacity of glycerol in vivo: The experiments were conducted in patients having diabetic ulcers covering a surface area of approximately 4 (±1.5) $cm^2$.2 ml of glycerol (Group 1, n=6 ulcers) or 2 ml of filmogen glycerol (Group 2, n=6 ulcers) was applied on the wound surface and the wounds were kept in a vertical position after application. Samples of wound fluid (100 μl) were collected at hourly intervals over a 6 h period, and the quantity of glycerol was measured.

The following results were obtained (see FIG. 2).

Results showed that under the experimental conditions of this study, nearly 92% of the normal glycerol was eliminated within 1 hour and 100% within 2 hours, compared to only 34% and 56% reduction for the filmogen glycerol. The activity of the filmogen glycerol lasted for 6 hours.

Example 4: Results of the Measurements of Tannin—Glycerol Binding and Production of Filmogen Glycerol As shown in the pharmacological study in example 3, among 42 tannin-rich plant extracts mixed with glycerol in different concentrations, either singly or in various associations, the following plant tannins (PCDs) showed different degrees of filmogenic qualities:

Very High filmogenic quality: 6 plant extracts were classified as very highly active: V. myrtillus, V. macrocarpon, V. vinifera, E. elder, C. sinensis and G. max as they increased the film retention duration between 200 and 300% compared to glycerol alone. Very high quality of glycerol film was obtained with: (1) the PCDs from Vaccinium myrtillus alone, as well as associations of PCD-rich plant tannins of (2) Vaccinium myrtillus (fruit extract)+Vaccinium macrocarpon (fruit extract); (3) Vitis vinifera (seed extract)+European elder (fruit extract); (4) Camellia sinensis (leaf extract)+V. myrtillus; (5) V. myrtillus+E. elder; (6) C. sinensis+V. vinifera+E. elder; (7) V. Vinifera+E. elder+Glycine max (seed extract); (8) V. macrocarpon+C. sinensis+V. vinifera; and (9) V. macrocarpon+C. sinensis+V. myrtillus+V. vinifera.

High filmogenic quality: 9 plant extracts were classified as highly active as they increased the film retention duration between 100 and 200% compared to glycerol alone: Acacia catechu (bark and whole plant), Tenacetum parthenium (flowers and leaves); Salix alba (whole plant); Salvia officinalis; Rosmarinus officinalis; Fraxinus chinensis, Gingko biloba; Ribes nigrum (fruit), and Opunitia Sp. (fruits) as well as synthetic polymers such as Aritan-A7, Ledosol CRP, and Blancotan SH2

Moderate filmogenic quality: 4 plant extracts were classified as moderately active as they increased the film retention duration between 10 and 99% compared to glycerol alone: Morus alba (fruits); Rubus sp. (fruits); Quercus sp (fruits, bark), Pinus sp (bark, fruit).

These results indicate that: 1. Tannins bind to glycerol; 2. Some plant tannins bind very strongly with the glycerol molecule, while others bind with a lesser strength. This shows that glycerol's binding with tannins is specific; 3. The binding of tannins to glycerol starts as soon as tannins are added to the glycerol; 4. Tannin dimers, trimers and pentamers show a stronger binding and filmogen effect, compared to polymers or big condensed tannins. This may be related to the fact that smaller tannin molecules have multiple possibilities to bind with glycerol. Nearly 50% PCD—glycerol binding occurs when both ingredients are mixed and stored, and the remaining 50% when the solution is applied as a thin film over the skin or mucosal surface. Synthetic polymers can also bind to glycerol molecules and improve the film retention duration of the glycerol film.

Based on these findings, the filmogen glycerol can be prepared by mixing glycerol or any other polyol solution with glycerol-binding plant PCDs.

Example 5: Examples of Preparations For Treatment of Skin and Mucosa Infections

Different filmogen glycerol preparations were prepared as detailed in Example 2. The percentages indicate the wt/wt of the dry PCD-rich plant extract.

1. Glycerol—69.22%, V. marcocarpon extract—0.18%, V. myrtillus extract—0.18%; Excipients: Honey—29.0%, Aqua—1.42% filled in 10 ml tubes to treat traumatic oral ulcers.

2. Glycerol—72.92%, *V. marcocarpon* extract—0.30%, *V. myrtillus* extract—0.36%; Excipients: Honey—12.0%, Aqua—14.42% filled in 20 ml spray for the treatment of oral mucositis.
3. Glycerol—74.265%, *V. vinifera* seed extract—0.48%, *S. nigra* (*E. elder*) fruit extract—0.32%; Excipients: Honey—12.0%, Aqua—12.935% filled in 30 ml sprays for throat application.
4. Glycerol—73.94%, *V. vinifera* seed extract—0.48%, *S. nigra* (*E. elder*) fruit extract—0.32%, *Glycine max* seed extract 0.07; Excipients: Honey—12.0%, Aqua—13.19%, filled in 20 ml sprays for throat application in children.
5. Glycerol—32.488%, *V. marcocarpon* extract—0.12%, *V. myrtillus* extract—0.12%, *C. sinensis* extract—0.22%, *S. nigra* (*E. elder*) fruit extract—0.10%; Excipients: Aqua—66.952%, filled in 15 ml plastic sprays for the treatment of rhinosinusitis.
6. Glycerol—68.66%, *V. myrtillus* extract—0.18%, *C. sinensis* extract—0.30%, Excipients: Honey—29.0%, Aqua—1.76%, Xanthan gum 0.1%, filled in 50 ml tubes for topical application on bedsore.
7. Glycerol—99.16%, *V. myrtillus* extract—0.18%, Citric acid qsp pH 4.5; Excipients: Aqua—0.66%, filled in 10 ml tubes with a canula for the treatment of vaginal dryness and infection.
8. Glycerol—72.06%, *V. vinifera* seed extract—0.18%. Excipients: Honey 27.0%, Aqua—0.66%. Xanthan gum 0.10%, filled in 100 ml tubes for topical application on skin injuries.
9. Glycerol—76.166%, *C. sinensis* extract—0.24%, *V. vinifera* seed extract—0.36%, *S. nigra* (*E. elder*) fruit extract—0.20%. Excipients: Honey—20.0%, Aqua—2.934%, Xanthan gum 0.10%, filled in 6 ml PET tubes for topical application on the lesions of cold sores (Labial herpes).
10. Glycerol—97.48%, *V. marcocarpon* extract—0.18%, *S. nigra* (*E. elder*) fruit extract—0.36%, Citric acid qsp pH 4.5; Excipients: Aqua—1.98%, filled in 10 ml tubes with a canula for vaginal application to treat genital herpes and bacterial vaginosis.
11. Glycerol—76.42%, *V. marcocarpon* extract—0.12%, *C. sinensis* extract—0.48%, *V. vinifera* seed extract—0.36%; Excipients: Honey—19.0%, Aqua—3.52%, filled in 50 ml tubes for topical application on the lesions of psoriasis, eczema and dermatitis.
12. Sorbitol—94.7%, *V. marcocarpon* extract—2.1%, *Acacia catechu* 3.2%, filled in 20 ml tubes for topical application on venous leg ulcers.
13. Glycerol—90.60%, *V. marcocarpon* extract—1.30%, *Salix alba*—5.0%; Excipients: Aqua—3.10%, filled in 50 ml tubes for topical application on diabetic ulcers.
14. Sorbitol—74.265%, *V. vinifera* seed extract—0.48%, *S. nigra* (*E. elder*) fruit extract—0.32%; Excipients: Honey—12.0%, Aqua—12.935%, filled in plastic 100 ml containers for topical application on skin burns.
15. Sorbitol—73.94%, *V. vinifera* seed extract—0.48%, *S. nigra* (*E. elder*) fruit extract—0.32%, *Glycine max* seed extract 0.07; Excipients: Honey—12.0%, Aqua—13.19%, filled in 10 ml syringes for topical application on chronic wounds.
16. Sorbitol—32.488%, *V. marcocarpon* extract—0.12%, *V. myrtillus* extract—0.12%, *C. sinensis* extract—0.22%, *S. nigra* (*E. elder*) fruit extract—0.10%; Excipients: Aqua—66.952%, filled in 50 ml sprays for throat application to treat the flu.
17. Xylitol—68.66%, *V. myrtillus* extract—0.18%, *C. sinensis* extract—0.30%, Excipients: Honey—29.0%, Aqua—1.76%, Xanthan gum 0.1%, filled in 100 ml tubes for the treatment of chronic dry ulcers.
18. Glycerol—95%, *V. myrtillus* extract—5.0%, Citric acid qsp pH 4.5, filled in 4 ml ovules for vaginal introduction to treat bacterial vaginosis.
19. Glycerol—50%, Xylitol—20%, *V. vinifera* seed extract—1.0%. Excipients: Honey 28.8%, Xanthan gum 0.20%, used to soak polyester bandages for application on chronic wounds.
20. 1 g of plant tannin preparation containing 400 mg extract of *V. vinifera*, 350 mg *V. macrocarpon*, 100 mg *V. myrtillus* and 150 mg powdered rice starch sprinkled on a 4×5 cm cotton gauze. First pure glycerol is applied on the injured surface (6 ml on 10 cm$^2$ surface of a chronic sore) and the wound surface is covered with the bandage, the sprinkled tannin part being directed towards the wound surface.
21. 5×5 cm cotton non-adhesive gauze-type dressings soaked in a solution containing glycerol (82%), 0.5% plant extract of *S. nigra* (*E. elder*) and 17.5% % honey and packed in aluminum bags. The gauze is directly applied topically on the injured surface.
22. Glycerol—76.0%, *C. sinensis* extract—0.5%, *V. vinifera* seed extract—0.5%, *S. nigra* (E. *elder*) fruit extract—0.5%. Excipients: Honey—22.5% mixed in a hydrogel and fixed on a cross-linked polymer surface (10 g per 10 cm$^2$ polymer surface) for topical application on bedsores, diabetic ulcers and venous leg ulcers.
23. Glycerol—97.48%, *V. marcocarpon* extract—2.10%, *S. nigra* (*E. elder*) fruit extract—0.42%, adsorbed on a flexible zinc oxide nanocomposite bandage as a wound healing dressing for chronic bedsores and diabetic ulcers.
24. Glycerol—68.66%, Aritan-A7—0.18%, *Fraxinus chinensis*—0.30%, Excipients: Honey—29.0%, Aqua—1.76%, Xanthan gum 0.1%, filled in 50 ml tubes for topical application on bedsores.
25. Glycerol—99.16%, *R. nigrum* extract—0.18%, Citric acid qsp pH 4.5; Excipients: Aqua—0.66%, filled in 10 ml tubes with a canula for the treatment of vaginal dryness and infection.
26. Glycerol—72.06%, *G. biloba* root extract—0.18%, Blancotan SH2 0.20%, Excipients: Honey 27.0%, Aqua—0.46%. Xanthan gum 0.10%, filled in 100 ml tubes for topical application on skin injuries.
27. Glycerol 99.5%, Ledosol CRP powder 0.5%, filled in 50 ml jars for topical application on psoriasis, eczema and dermatitis skin lesions.
28. Glycerol 30%, Honey 69.5%, dried extract of *Fraxinus chinensis* 0.50%, filled in 50 ml containers for topical application on the throat surface to treat viral throat and sinus infections.

Example 6: Cryopreservation Experiments;
Comparative Study on Glycerol Versus Filmogen Glycerol The aim of this study was to compare the protective effects of glycerol alone or in association with tannins or polymers capable of forming a glycerol film over the live tissue surface, and to evaluate the effects obtained on cell survival.
Live Cells and Tissues Used:

Primary cultures of vascular human smooth muscle cells (SMCs), skin fibroblasts, rat kidney epithelial cells, MDBK and MDCK cell lines were grown in 25 cm$^2$ plastic tissue culture flasks.

Cells were dispersed with trypsin—EDTA solution, washed with medium, and a cell suspension containing 1×10$^7$ cells/ml was prepared. Suspensions of human blood lymphocytes were also prepared as samples of non-adherent cells. Similarly, fresh live human skin samples collected for hospitals were cut into 1 cm$^2$ pieces and two pieces of each skin sample were cryopreserved in different mediums as given below.

Four freezing mediums were prepared in DMEM (Dubelco's Minimum Essential Medium) containing either: (1) 5% DMSO, 10% FCS and culture medium qsp 100 ml; (2) 2% DMSO+10% serum and culture medium qsp 100 ml; (3) glycerol 20%, FCS 10%, 2% DMSO and culture medium qsp 100 ml; or (4) glycerol 20% plant PCDs 1%, FCS 10%, DMSO 2% and culture medium qsp 100 ml called filmogen glycerol. Mediums were stored at 2° to 8° C. until use. Note that the appropriate freezing medium depends on the specific cell line.

Cell suspensions were centrifuged at approximately 100-200×g for 5 to 10 minutes and the supernatant was decanted without disturbing the cell pellets. Cell pellets were re-suspended in cold freezing medium at densities of 1×10$^8$ cells per ml. Aliquots of the cell suspension were dispensed into cryogenic storage vials and frozen in a controlled-rate freezing apparatus, decreasing the temperature approximately 1° C. per minute up to −70° C. Tissue and cell culture vials were then transferred to liquid nitrogen containers (−196° C.) and kept for a 6-month period. The same technique was followed for the skin grafts.

For thawing, ampoules were removed and left at room temperature for approx. 1 minute and then transferred to a water bath at 37° C. for 2-3 minutes until fully thawed. Ampoules were wiped in 70% alcohol prior to opening in a sterile environment. Cells were diluted in 10 ml DMEM containing 5% FCS, centrifuged, pelleted, re-diluted in culture medium and the number of live cells was determined using trypan blue and MTT stains.

The skin grafts processed in a similar fashion except that the grafts were cut into 5 slices, introduced in 25 cm$^2$ tissue culture flasks containing 15 ml cell growth medium with 10% FCS and grown for a period of 10 days. After 10 days of culture, the growing graft cells were dispersed with trypsin—EDTA solution, a cell suspension was prepared and the number of live cells was counted.

Results:

Mean number of live cell culture cells: (1) 5% DMSO, 10% FCS in culture medium=65.2%; (2) 2% DMSO+10% serum in culture medium =62.6%; (3) 20% glycerol, 10% FCS and 2% DMSO in culture medium=68.4%; and (4) 20% glycerol containing 1% plant PCDs, 10% FCS, 2% DMSO in culture medium called filmogen glycerol=91%.

Mean number of live skin graft cells: (1) 5% DMSO, 10% FCS in culture medium=51.1%; (2) 2% DMSO+10% serum in culture medium=54.9%; (3) 20% glycerol, 10% FCS and 2% DMSO in culture medium=63.3%; and (4) 20% glycerol, 1% plant PCDs from *V. marcocarpon* (0.5%) and *R. nigrum* (0.5%), 10% FCS, 2% DMSO in culture medium called filmogen glycerol=83.8%.

Conclusion: Filmogen glycerol is much more efficient, compared to glycerol alone, for cryopreservation of individual dispersed cells and tissue grafts.

Example 7: Examples of Cryopreservative Filmogen Glycerol

Different preparations were prepared as detailed in Example 2. The percentages indicate the wt/wt of the dry PCD-rich plant extract.

1. Glycerol 20%, Plant PCDs of *V. myrtillus* 0.5%, *A. catachu* 0.4%, and *S. alba* 0.1%; DMSO 5.0%, fetal bovine serum 20%, culture medium qsp 100 ml used to store dispersed live cells.
2. Glycerol 20%, Plant PCDs 1% (of *V. marcocarpon* 0.5% and *R. nigrum* 0.5%), FCS 10%, DMSO 2.0% in culture medium qsp 100%.
3. Glycerol 10%, Plant PCDs of *V. vinifera* seeds 1.0% and *E. elder* 0.5%, DMSO 2.0%, fetal bovine serum 10%, culture medium qsp 100 ml, used to store skin grafts before grafting and transport.

Example 8: In Vitro Osmotic Properties of Glycerol Alone Compared to Glycerol Containing 1% Association of Plant PCDs as Per the Preparation n° 2 in Example 5 (code—Orosol)

In the absence of in vivo models to mimic the osmotic exudation of hypotonic liquid from the oral or vaginal mucosa, a cell culture model of human epidermis was used which contains normal human epithelial cells grown on a polycarbonate filter in an air/liquid phase. Under optimal conditions, a multilayered cell culture, equivalent to the mucosal surface is obtained on a polycarbonate support. This support is placed on a sponge in contact with a defined amount of culture medium. The medium diffuses into the sponge and the filter, and supplies nutrients as well as hydration to the cells. Under these conditions, the cell culture can be kept alive for at least a week.

To create an experimental model of mucosa dryness, we inserted one or two extra filters between the cells and the sponge, thereby reducing the amount of liquid medium available to the cells. In absence of hydration, cells die, and the cell mortality can be measured with a vital dye MU. Cell mortality is proportional to the culture surface's dryness.

If an osmotically active, hypertonic solution is applied on the epidermal surface exposed to dryness, the culture medium is attracted towards to epidermis due to osmosis and increases the amount of medium available to the cells. Cell survival is therefore proportional to the extent of osmosis and cellular hydration.

The aim of this study was to evaluate the hydrating properties of filmogen glycerol compared to regular glycerol. The product was applied on the surface of the normal (no filter), slightly dehydrated (1 filter) or severely dehydrated (2 extra filters) epidermis (20 μl), and cells were incubated at 37° C.-5% CO$_2$ for one week. Each epidermis was washed by stirring the culture in culture medium for 20 seconds on days 1, 3 and 5, and cell viability was measured on day 7 using MU staining.

Mean score of cell survival after 1-week culture was as follows:

1. Normally humidified cultures (no filter): 100%
2. Partially dehydrated controls without product: 43.11%
3. Severely dehydrated cultures without product: 11.57%
4. Partially dehydrated cultures with glycerol: 62.3%
5. Severely dehydrated cultures with glycerol: 43.15%
6. Partially dehydrated cultures with filmogen glycerol: 89.46%
7. Severely dehydrated cultures with filmogen glycerol: 77.89%

Conclusion: Filmogen glycerol remains on the surface of the epidermis over a longer period of time compared to normal glycerol, with higher osmotic effects, and protects the cells against dehydration.

Example 9: In Vivo Rat Wound Healing Properties of Filmogen Compared to Normal Glycerol Methods of Experimental Lesion Induction The rat dorsal skin was shaved and 3 circular lesions, 0.8 mm in diameter and depth, were made to the hypodermis with a dermatome. 0.2 ml of each test product was applied on each lesion for 7 consecutive days. Lesion diameter was measured every day and mean values were compared.
Test Product:
Group 1: Distilled water; Group 2: Glycerol alone; Group 3: Filmogen glycerol as per the example N° 6. (10 rats in each group).
Results:
Mean lesion size (diameter/day/lesion during 7 days) in distilled water group=3.32 $cm^2$; in glycerol group=2.95 $cm^2$ and in the filmogen glycerol group=2.03 $cm^2$.
Conclusion:
Although glycerol alone does accelerate healing, the healing rate was much faster with the application of filmogen glycerol.
Stability of the Glycerol and Tannin Preparations:
Studies were conducted to evaluate the stability of preparations cited in the examples over 36 months of storage at 30° C.±2° C. and at 40° C.±2° C. The preparations were stable for a minimum period of 36 months.
Contents-Container Interactions:
Preparations cited in the examples were filled into plastic (PE, PET) tubes and aluminum containers and the contents were analyzed at regular intervals to evaluate any interaction between the contents and the containers. Infrared spectrophotometry analyses of samples just after preparation and after 12 months of storage at 37° C. indicated the absence of any interaction between the contents and the containers.
In-Use Stability:
Samples of the compositions cited in the examples were studied for decomposition or contamination during in-use period. The results obtained validated the product in-use stability for a period of 1-3 months.
Cytotoxicity:
The cytotoxicity of filmogen glycerol, evaluated according to NF-ISO 10993 guidelines showed that the product is not cytotoxic up to a concentration of 5% in the culture medium of L929 cells.
Hypersensitivity:
This study was conducted in accordance with the requirements of the FDA Good Laboratory Practice (GLP) Regulations (21 CFR, Part 58, Apr. 1, 2005) and the OECD Good Laboratory Practices, reference ENV/MC/CHEM (98) 17 adopted by decision of the Council of Nov. 26, 1997 using examples of the preparations N° 2, 3, and 5.
The product was injected intra-dermally, as well as applied topically directly on the shaved G. pig skin with a patch, to evaluate local reaction and delayed hypersensitivity. For comparison, an identical negative control test was performed with 0.9% NaCl solution by injecting the solution intra-dermally and by topical application. The products sensitized the skin by intradermal injection but topical application did not induce sensitization.
Oral Toxicity in Vivo:
The samples of filmogen glycerol as per the example N° 2, 7, 8 and 20 were administered to rats at a dose of 5 g/kg body weight. The study was conducted according to GLP norms. In the absence of any abnormality, the acute lethal dose was estimated above 5 g/kg for all the products tested.
Topical Irritation:
The studies were performed using examples of the test product composition N° 2, 7, 9, 10 and 12 as per the protocols for skin and in vitro BCOP eye irritation tests published in the official journal of French Republic of 21 Feb. 1982. The primary cutaneous irritation index was below 0.50 and the products were classified as non-irritant to the skin. The mean Bovine Corneal Opacity Index was between 10 and 25 for all the products and therefore the products were classified as slightly irritant to the eyes.

Example 11: Clinical Efficacy

Different preparations were prepared as per the examples of compositions given in the text and the clinical efficacy of the compositions was evaluated in patients suffering from skin or mucosa pathologies. The summaries of the studies are given below.
Study 1: Therapeutic Efficacy of Glycerol Alone Versus Filmogen (Preparation N° 11 of Example 5 called VB-DERM) For the Treatment of Psoriasis, Eczema and Dermatitis.
A 6-week long, single blind trial on 107 patients suffering from skin lesions of Psoriasis, Eczema & Dermatitis (PED) was performed, in which the clinical efficacy of composition as per the preparation N° 11 as per Example 5 was compared with glycerol alone for the treatment of skin lesions due to Psoriasis, Eczema or Dermatitis (PED). 56 patients were treated with filmogen glycerol preparation VB-DERM (filmogen glycerol group) and 51 with glycerol alone (control group). The product was applied topically, twice daily for a period of 6 weeks. Lesions were rated on a scale of 0 to 4 on weeks 0, 1, 2, 4 and 6.
All throughout the study, very positive results of filmogen glycerol preparation (VB-DERM) efficacy on Psoriasis, Eczema, and Dermatitis have been observed.
Analyzing the scores recorded at regular time intervals over a 6-week span clearly proved that filmogen glycerol is much more effective for the treatment of PED lesions compared to glycerol alone (FIGS. 3, 4 and 6). The wound cleaning and healing efficacy of filmogen glycerol was statistically significant ($p<0.005$) in treating all symptoms associated with those diseases: erythema & pruritis, oedema, dryness, oozing, scaling & crusting, and itching. The quality of life as assessed by the investigators and the patients, right from the second week after the start of treatment, was also significantly improved (FIG. 5).
These results indicate that filmogen glycerol remains on the surface of the PED lesions for a much longer period of time thereby keeping the injury clean of all the free contaminants (dead cells, cell debris, proteolytic enzymes, MMPs, cytokines, interleukines, interferons, viruses, bacteria, dust particles) and restoring normal skin cell production. Filmogen glycerol is thus much more highly active compared to non-filmogen glycerol for the treatment of skin diseases involving excessive skin growth, presence of contaminants in the lesions, involvement of multiple free-floating impurities such as dead cells, cytokines, MMPs, and other protein molecules at the site of injury. These contaminants are permanently removed from the lesion, creating a favorable ground for normal skin growth.
Study 2: Therapeutic Efficacy of Glycerol Alone and Filmogen Glycerol (composition as per the preparation N° 10 of example 5 (HG-VB)) For the Treatment of Genital Herpes An open label, single-arm, prospective, multicentric, pilot study was conducted to evaluate the efficacy of filmogen glycerol (HG-VB), compared to normal standard glycerol, in women suffering from genital herpes and infection.

60 women having visible lesions of genital herpes were treated with HG-VB (10 ml per day) for 14 consecutive days. Product was administered daily into the vaginal cavity and the symptoms of genital herpes were evaluated before treatment and on days 1 (2 h), 4, 7, and 14. Smears from genital lesions were also collected to evaluate the number of virus-loaded multinucleated giant cells using Tzanck test. 20 women were treated only with glycerol under identical clinical conditions.

Results: Statistically significant reduction in vaginal itching, redness, pain, dryness, discharge, presence of blisters, and normalization of vaginal pH was observed right after 2 h of $1^{st}$ application of HG-VB compared to the treatment with glycerol alone. The results of this study clearly proved that a filmogen glycerol continues draining hypotonic liquid from the inner parts of the vaginal cavity over a period of 6-8 hours and cleans all the contaminants, compared to glycerol alone with a shorter duration (0.5 to 1 h) of action.

Study 3: Efficacy of Glycerol Alone and Filmogen Glycerol (glycerol in association with PCD-rich plant extracts as per the preparation N° 9 of example 5 (HL-VB)) in Eliminating Free Virus Particles Present on the Surface of Labial Herpes Lesions An open label, single arm, prospective, multicentric, pilot study was conducted on 60 patients having open labial herpes lesions. 30 patients were treated with normal glycerol and 30 with HL-VB by applying a few drops of the products, in each group identically, twice daily for a maximum period of 14 consecutive days. Labial lesion smears were collected and mean virus concentration was measured by quantifying the number of multinucleated virus-infected giant cells in each lesion using Tzank test, and the mean amount of free virus particles was determined in both groups.

The mean amount of free virus particles was >750, 635 (±17.51), 542 (±22.35.), and 522 (±13.50) in glycerol treated group compared to 465 (±10.8), 359 (±6.35), 226 (±10.22), and 0.0 on days 1, 4, 7 and 14, respectively. These results indicate that HL-VB, i.e. glycerol containing PCDs or filmogen glycerol, exerts its effects over a longer period of time than glycerol alone.

Study 4: Efficacy of Glycerol Alone and Glycerol in Association With PCD-Rich Plant Extracts, Called Filmogen Glycerol (composition as per the preparation N° 5 of example 5 (G-PCD)), to Break Open the Bacterial Biomembrane Blocking the Sinus Openings in Patients Suffering From Rhino Sinusitis A 21-day controlled clinical trial of G-PCD compared to glycerol alone in patients suffering from acute symptoms of nasal sinus infection was performed.

The aim of this study was to evaluate the sinus-opening efficacy of G-PCD solution (32% glycerol, 1% plant PCDs in water) as per the example N° 5, compared to glycerol alone (32% glycerol in water). Among 127 patients suffering from acute and chronic sinusitis 109 were selected for the study. 58 patients were treated with G-PCD and 51 with glycerol. Products were administered as sprays (3 at each treatment application), 2-3 times per day for a maximum period of 21 days.

The parameters studied were: 1. Effect on nasal congestion and runny nose; 2. Effect on pain upon pressure around the nasal sinus surface; 3. Overall condition of the patient with respect to sinus infection; and 4. The influence on antibiotic therapy. Results recorded after 30 minutes, 3 days and 7 days, showed a significantly greater symptom reduction in the G-PCD group compared to glycerol group for nasal congestion (−31.02%, −57.23% and −73.79% compared to −20.40%, −19.09% and −30.25%), sinus pain (−6.91%, −79.02% and −85.18% compared to −1.69%, −8.36% and −53.36%), and overall rhinosinusitis condition (−4.15%, −69.84% and −79.89% compared to −22.56%, +3.52% and −17.62%) (FIG. 7). The intensity of runny nose was increased by as much as 164.79% in the G-PCD group compared to only 31.71% in the glycerol group within 30 minutes of first product administration. These results indicate that G-PCD exerts a very high osmotic pressure compared to glycerol under identical conditions, leading to the breakdown of the biofilm and opening of the sinuses. Only 21% patients in the G-PCD group required antibiotic therapy for an average 7.41 days compared to 40% in the glycerol group for a period of 10.5 days (FIG. 8)

These results clearly indicate that filmogen glycerol remains over the nasal mucosa surface for a longer period of time compared to the standard glycerol solution.

Study 5: Comparative Film-Forming and Osmotic Properties of Glycerol Alone Compared to the Glycerol Containing 1% Plant PCDs (filmogen glycerol composition as per the preparation N° 2 of example 5 (Orosol)) on Oral Mucositis Lesions Chemotherapy- and radiotherapy-induced oral mucositis lesions show a highly damaged oral mucosa, with infection and the presence of toxic chemicals in the lesion. This causes severe pain, burning sensation, and difficulty in eating. Among a total of 69 patients enrolled in the study, 48 were treated with the Orosol solution and 21 with glycerol as a spray. Product was applied 4-5 times per day for a period of 28 days. The grade of overall mucositis, intensity of pain and burning sensation, formation of new ulcers and effect on eating impairment were evaluated before treatment, 30 minutes after first product application and on days 1, 2, 3, 4, 7, 14, 21 and 28. A statistically significant difference in mucositis healing was observed in the Orosol group compared to the glycerol group (FIG. 9). The duration of Orosol activity was nearly 3 times longer compared to glycerol alone in the control group, with proportional increase in the healing effects. Filmogen glycerol attracts hypotonic liquid for a much longer period of time, cleans the lesion, and helps promote recovery.

The results of these 5 clinical studies prove that:

1. Plant PCD-containing glycerol forms a long lasting highly osmotic film over the injured surfaces and mucosa compared to glycerol alone.

2. The cleaning effects on the injured surface are directly proportional to the duration of retention of the osmotic glycerol film over the injury.

3. The osmotic exudation of hypotonic liquid eliminates all the free-floating contaminants, irrespective of the nature of the contaminant, due to the non-pharmacological but mechanical properties of the osmotically active film.

4. PCD-containing filmogen glycerol is safe and non-irritant.

The invention claimed is:

1. A method of improving the mechanical resistance and enhancing the retention time of a filmogen glycerol film over live cells which keeps the film intact over the live cells comprising mixing glycerol with a plant tannin which has the capacity to bind to glycerol molecules to form a solution and applying the solution to the live cells, wherein the plant is selected from the group consisting of *Vaccinium myrtillus, Vaccinium macrocarpon, Vitis vinifera,* European elder, *Camellia sinensis, Glycine max, Acacia catechu, Fraxinus*

*chinensis, Gingko biloba, Ribes nigrum, Tenacetum parthenium, Salix alba, Salvia officinalis, Rosmarinus officinalis,* an *Opuntia* sp., *Moms alba,* a *Rubus* sp, a *Quercus* sp., a *Pinus* sp., and *Rheum emodi.*

\* \* \* \* \*